United States Patent
Skerl et al.

(10) Patent No.: US 8,965,493 B2
(45) Date of Patent: Feb. 24, 2015

(54) ELECTROMEDICAL IMPLANT AND MONITORING SYSTEM

(75) Inventors: Olaf Skerl, Bad Doberan (DE); Michael Lippert, Ansbach (DE); Gerald Czygan, Buckenhof (DE)

(73) Assignee: Biotronik SE & Co. KG, Berlin (DE)

( * ) Notice: Subject to any disclaimer, the term of this patent is extended or adjusted under 35 U.S.C. 154(b) by 909 days.

(21) Appl. No.: 13/040,926

(22) Filed: Mar. 4, 2011

(65) Prior Publication Data

US 2011/0224520 A1    Sep. 15, 2011

Related U.S. Application Data

(60) Provisional application No. 61/311,792, filed on Mar. 9, 2010.

(51) Int. Cl.
  *A61B 5/04*  (2006.01)
  *A61B 5/053*  (2006.01)
  *A61B 5/00*  (2006.01)

(52) U.S. Cl.
  CPC ............ *A61B 5/0535* (2013.01); *A61B 5/6846* (2013.01); *A61B 5/7207* (2013.01); *A61B 2562/0209* (2013.01); *A61B 2562/043* (2013.01)
  USPC ........................................ 600/513

(58) Field of Classification Search
  USPC .......................... 600/345, 377, 374
  See application file for complete search history.

(56) References Cited

U.S. PATENT DOCUMENTS

| | | | |
|---|---|---|---|
| 3,608,543 A * | 9/1971 | Longini et al. ............... | 600/536 |
| 4,674,518 A | 6/1987 | Salo | |
| 5,331,966 A | 7/1994 | Bennett et al. | |
| 5,743,856 A | 4/1998 | Oka et al. | |
| 6,360,123 B1 * | 3/2002 | Kimchi et al. ............... | 600/547 |
| 6,748,262 B2 | 6/2004 | Harada et al. | |
| 7,029,447 B2 | 4/2006 | Rantala | |

(Continued)

FOREIGN PATENT DOCUMENTS

DE         3629587 A1    3/1987
WO    WO 2004/047638 A1    6/2004

(Continued)

OTHER PUBLICATIONS

DE 3629587 corresponds to US 4674518, Mar. 12, 1987.

*Primary Examiner* — Catherine Voorhees
*Assistant Examiner* — Roland Dinga
(74) *Attorney, Agent, or Firm* — Muncy, Geissler, Olds & Lowe, P.C.

(57) ABSTRACT

An electromedical implant for monitoring a thoracic property of a living being is provided that includes a detector arrangement including an impedance measuring unit and an electrode arrangement, which are equipped to capture a measurement signal associated with the thoracic property in the form of an impedance signal; a monitoring arrangement, which is connected to the detector arrangement and equipped to generate a parameter from the measurement signal that is indicative of the thoracic property, and an evaluation unit, which is connected to the monitoring arrangement and equipped to determine an evaluation result regarding the thoracic property based on the parameter. According to the invention, the electrode arrangement comprises at least a plurality of mutually isolated electrodes, which are disposed on the housing and operatively connected by way of the impedance measuring unit and which can be separately controlled, wherein an electrode body has a strip shape.

21 Claims, 2 Drawing Sheets

(56) References Cited

U.S. PATENT DOCUMENTS

| | | | |
|---|---|---|---|
| 7,970,462 B2* | 6/2011 | Lefkov et al. | 600/547 |
| 8,162,841 B2* | 4/2012 | Keel et al. | 600/486 |
| 2004/0225329 A1 | 11/2004 | Wagner et al. | |
| 2005/0080463 A1* | 4/2005 | Stahmann et al. | 607/62 |
| 2005/0261743 A1* | 11/2005 | Kroll | 607/8 |
| 2006/0041280 A1* | 2/2006 | Stahmann et al. | 607/17 |
| 2006/0135886 A1* | 6/2006 | Lippert et al. | 600/547 |
| 2008/0065183 A1* | 3/2008 | Whitehurst et al. | 607/116 |
| 2008/0125826 A1* | 5/2008 | Belalcazar et al. | 607/17 |
| 2008/0183225 A1 | 7/2008 | Adamski et al. | |
| 2008/0234591 A1 | 9/2008 | Scinicariello et al. | |
| 2008/0300504 A1* | 12/2008 | Lefkov et al. | 600/547 |
| 2009/0012416 A1* | 1/2009 | Belalcazar et al. | 600/529 |
| 2009/0062667 A1 | 3/2009 | Fayram et al. | |
| 2009/0326599 A1* | 12/2009 | Hatlestad et al. | 607/17 |

FOREIGN PATENT DOCUMENTS

| | | |
|---|---|---|
| WO | WO 2005/010640 A2 | 2/2005 |
| WO | WO 2009/035596 A1 | 3/2009 |

* cited by examiner

Fig. 2

ELECTROMEDICAL IMPLANT AND MONITORING SYSTEM

This nonprovisional application claims priority to U.S. Provisional Application No. 61/311,792, which was filed on Mar. 9, 2010, and which is herein incorporated by reference.

BACKGROUND OF THE INVENTION

1. Field of the Invention

The present invention relates to an electromedical implant for monitoring a thoracic property of a living being, wherein the implant has a housing. The invention further relates to a monitoring system including the electromedical implant.

2. Description of the Background Art

An electromedical implant can be purely a monitoring implant, or a monitoring and therapy implant. Contrary to therapy implants, such as implantable cardiac stimulators or the like, an electromedical implant for monitoring a thoracic property of a living being (patient), which is referred to as a monitoring implant, provides no therapy options. A monitoring implant can also be useful and important for patients having no therapy indication in order to draw conclusions about the health of the patient by monitoring a thoracic property. For example, an indication for electrotherapy may not be apparent, or a type of electrotherapy prior to conducting the same may not be specifiable in detail, until the patient has been monitored for an extended period using the monitoring implant.

Existing approaches for monitoring a thoracic property, which is to say the pulse transit time, of a living being largely employ non-invasive systems, as those which are described, for example, in U.S. Pat. Nos. 7,029,447 or 6,748,262 or 5,743,856 for monitoring cardiac or epithoracic, peripheral blood flows. Non-invasive systems, however, are cumbersome to handle when it comes to monitoring a thoracic property of a living being for an extended period. On the other hand, a cardiac invasive system, as that described in DE 36 29 587 A1, which corresponds to U.S. Pat. No. 4,674,518, is not an option for a patient having no therapeutic indication. The implantation of probes in the heart, for example for determining an ECG signal using a cardiac stimulator, is associated with risks for the patient and complex. At the same time, patients without indication for electrotherapy constitute a significant portion of patients suffering from cardiac insufficiency.

The desire is therefore to provide an electromedical implant for monitoring a thoracic property of a living being, which also enables long-term, comparatively simple monitoring without requiring cardiac invasion.

An electromedical implant mentioned at the beginning is known, for example, from US 2009/0062667 A1, wherein ultimately, for monitoring an arterial blood pressure a pulse transit time is determined from the pulse peak arrival times of two signals. Using subcutaneously implanted electrodes, a first signal in the form of an electrocardiogram is determined, which is indicative of an electrical activity of a patient's heart, which is to say the blood ejected from the heart. In addition, a sensor in the form of a photoplethysmography sensor implanted in the pectoral region is used to obtain corresponding signal which is indicative of a mechanical activity of a patient's heart, which is to say the arrival of a blood pulse in the pectoral region. This concept can be implemented as an implantable monitor having no electrotherapy device.

U.S. Pat. No. 5,331,966 discloses an electromedical implant comprising a detector arrangement, which includes an array of relatively closely spaced subcutaneous electrodes for detecting electrical cardiac signals, wherein a selected electrode pair for recording what is referred to as a far-field electrocardiogram is provided. The array of electrodes is attached on or in the vicinity of the implant outside of a patient's heart, wherein the electrodes are disposed in a circular shape and in a triangular arrangement on the surface of the implant in order to record a vectorial subcutaneous far-field electrocardiogram.

US 2008/0234591 A1 and US 2008/0183225 A1 disclose an electromedical implant having a shroud assembly which surrounds the implant and again comprises three electrodes having an oval shape, which are disposed on a narrow side of the implant and provided for recording an extracardiac far-field cardiogram.

US 2004/0225329 A1 discloses an electromedical implant having a plurality of subcutaneous electrodes, which are disposed as part of an array on a lateral surface of the implant and interact with surface electrodes attached to the thorax of the patient for recording a subcutaneous electrocardiogram.

While the above approaches of subcutaneous electromedical implants, in principle, have proven useful for monitoring a thoracic property of a living being, they are in need of improvement.

SUMMARY OF THE INVENTION

It is therefore an object of the invention to provide an electromedical implant, particularly a monitoring implant, for monitoring a thoracic property of a living being, by which a thoracic property of the living being can be determined in a comparatively simple and yet reliable manner. Further, the implant should be as compact and as easy to produce as possible.

It is a further object of the invention to provide a monitoring system utilizing the electromedical implant, by which the thoracic property, particularly additional patient values which can be derived from the thoracic property, can be monitored and retrieved lastingly or over an extended period. In particular, a monitoring system is to be able to make patient values reported by the electromedical implant available for visualization. In this way, the condition of a patient can be derived particularly easily.

With respect to the electromedical implant, the object of the invention is achieved by an electromedical implant, wherein according to an embodiment of the invention the following is provided: a detector arrangement comprising an impedance measuring unit and an electrode arrangement, which are equipped to capture a measurement signal associated with the thoracic property in the form of an impedance signal; a monitoring arrangement, which is connected to the detector arrangement and equipped to generate a parameter from the measurement signal that is indicative of the thoracic property, and an evaluation unit, which is connected to the monitoring arrangement and equipped to determine an evaluation result regarding the thoracic property from the parameter. Whereby, the electrode arrangement comprises at least a plurality of mutually isolated electrodes, which are disposed on the housing and operatively connected by way of the impedance measuring unit and which can be separately controlled, wherein an electrode body has a strip shape.

An impedance signal in the present invention can be understood to be a signal from a voltage sampling having a known current impression, or a signal from a current sampling having a known voltage impression, or a similar signal, from which the impedance between two poles of the electrode arrangement, which is to say the impedance signal, can be deduced. This applies in particular to the impedance at a defined frequency of an electric current or an electric voltage. The impedance can also be determined from a pulse-shaped alternating current or a pulse-shaped alternating voltage. Advantageously, for this purpose the electromedical implant has an advantageously designed impedance measuring unit. The impedance measuring unit preferably includes an exciter module for delivering an electric current via the electrode arrangement and a sampling module for receiving a voltage via the electrode arrangement. Conversely, the exciter module can also be used for delivering a voltage via the electrode arrangement and the sampling module can be used for receiving a current via the electrode arrangement. By delivering a current or a voltage, it is impressed on the surrounding tissue. Conversely, a voltage or current borne by the surrounding tissue can be sampled. A parameter of the thoracic property or evaluation results of an evaluation of the parameter can advantageously be provided by the electromedical implant to a monitoring system (200). For this purpose, the electromedical implant preferably comprises a communication module for the wireless transmission of the evaluation results from the implant to the monitoring system.

On an overall basis, the invention is based on the deliberation that an impedance measurement is particularly advantageously suited to establish conductivity changes in the thorax of a living being. In addition, the invention is based on the deliberation that conductivity changes in the thorax of a living being are suited to detect changes in the fluid condition of the living being at an early stage. The electromedical implant is therefore suited particularly advantageously for monitoring a fluid condition in the thorax of a living being. In this way, fluid accumulations, edemas, or the like in the thorax, particularly in the lungs, and the changes thereof, can be effectively monitored at an early stage. The invention is based on the realization that an impedance measurement according to the invention is best implemented using an electrode arrangement, which comprises a plurality of mutually isolated electrodes—preferably regularly or irregularly in a defined structure. Since the electrodes are operatively connected by way of the impedance measuring unit, they can be activated, preferably as part of a regular structure, particularly flexibly and as needed individually, in pairs, or in groups, and can be used for the impedance measurements. Conductivity changes in the thorax of the living being can thus be monitored using individual or several redundant or mutually complementary combinations of impedance measurements using different electrodes of a regular structure. In principle, very detailed assessments can be made in this way about conductivity changes in different regions of the thorax. In addition, the invention is based on the realization that an electrode body, which is to say the surface section of an electrode provided for contact with the tissue or blood, which has an elongated shape is particularly suited to determine a reliable impedance signal. It has been shown that the elongated shape in particular enables a determination of the impedance signal largely independent of the position of the electromedical implant.

In the context of an embodiment, the electromedical implant may have an anchoring device. An anchoring device is advantageously provided in the form of a sewing lug, a screw, an anchoring structure, or as another means, in order to fix the electromedical implant in the position thereof after subcutaneous implantation. In this way, in such an implanted state, it is not only possible to stabilize the position of the electromedical implant and prevent a migration thereof, but also to avoid uninterpretable results in the measurement signals due to movements. The anchoring device can be designed reversibly, which is to say such that the anchoring device can be released, if possible without injury to the living being. This allows the implant to be removed from the body of the living being, if needed.

The electromedical implant in particular provides the possibility to determine a thoracic fluid condition of a living being, in particular a fluid accumulation in the thorax of the living being, preferably in the lungs. The electromedical implant also provides the possibility to capture a measurement signal associated with the cardiac blood flow and a measurement signal associated with the epithoracic, peripheral blood flow of the patient in a particularly simple and reliable manner.

In an embodiment, an impedance measurement according to the above general concept for determining conductivity in the thorax of a living being can be carried out using the electromedical implant according to the invention. The implant has proven to be particularly advantageous for monitoring a thoracic property in the form of a cardiac blood flow and/or an epithoracic, peripheral blood flow. For this purpose, the detector arrangement can be equipped to capture a first measurement signal associated with the cardiac blood flow and a second measurement signal associated with the epithoracic, peripheral blood flow. In addition, the monitoring arrangement connected to the detector arrangement is equipped to generate, from the first measurement signal, a first parameter that is indicative of a time at which blood is ejected from the heart, and/or equipped to generate, from the second measurement signal, a second parameter that is indicative of a time of a blood pulse in the thoracic tissue with which the blood ejection is associated. The evaluation unit connected to the monitoring arrangement is equipped to generate a pulse transit time from the first parameter and the second parameter. In this variant, the impedance measuring unit and the electrode arrangement are equipped to detect the first and/or second measurement signals in the form of an impedance signal.

The first and second parameters each are parameters indicative of thoracic impedance. A parameter in the present invention shall be understood as any quantifiable characteristic of a measurement signal. In the present invention, a parameter is indicative of a time in particular when it defines a characteristic of the measurement signal which can be sufficiently limited in terms of time. In principle, the parameter can be generated directly from the measurement signal, or also from a signal obtained from the measurement signal, such as by filtration or mathematical derivation or the like. A measurement signal is present in the form of an impedance signal in particular when it is derived directly or indirectly from a signal obtained on the basis of an impedance measurement.

In order to achieve the objects, according to the invention a monitoring system is proposed, comprising the electromedical implant including the above described communication module, wherein the monitoring system further comprises: a receiving unit for receiving the evaluation signal; and a memory unit for the evaluation result.

The evaluation result is made available for further processing by the memory unit, which can be provided on the implant or on the receiving unit. In this way, the evaluation result can be stored and queried by the physician during a follow-up examination using a suitable interrogation device. However, a query can also be conducted directly by the patient, or by an authorized service center.

The concept of the invention advantageously makes it possible to make the thoracic property monitored by the implant, and the evaluation result determined therefrom, available for further analysis. In this way, additional patient values can be generated, indicating a patient condition. For this purpose, suitable further processing units, or interrogation units, can be provided as part of the monitoring system, which preferably are able to communicate in a wireless manner with the monitoring system and/or the implant, in particular with the receiving unit, and/or are able to access the memory unit.

A telemetric connection of the electromedical implant to the monitoring system via the communication module enables automatic remote monitoring of the living being by way of the electromedical implant. The patient/living being can thus be monitored remotely by the physician or a service center, and alarm conditions can be generated based on the transmitted evaluation results, which are displayed in the service center and/or directly at the physician's practice. In this way, a physician can be notified of critical conditions of a living being/patient via the service center, for example directly, or by way of further communication device or system, such as an Internet platform, SMS, e-mail, fax or the like.

Monitoring a lung condition, in particular the pulmonary fluid content, has proven particularly advantageous. On a general note, the detection of serious changes in a thoracic property, primarily a property of the lungs, in particular increasing fluid accumulations, can be used to detect developing cardiac decompensation. The goal can also be the early detection of developing edemas, particularly lung edemas. The latter frequently have a cardiac cause, such as the result of decompensation, but may also have other causes. In principle, monitoring a thoracic fluid condition of a patient has proven advantageous. This applies in particular to patients with renal insufficiency, kidney transplants, or patients with diuresis. Imminent cardiac and other severe deterioration of the patient's health can therefore be detected at an early stage.

In addition, monitoring a cardiac blood flow and an epithoracic, peripheral blood flow of a living being have proven to be advantageous for determining a pulse transit time. A pulse transit time shall be understood as the time difference between a time at which blood is ejected from the heart of a patient and the time of a blood pulse in the thoracic tissue, wherein the blood pulse in the thoracic tissue occurs with time delay and is caused by the ejected blood.

A reduced pulse transit time, for example, is an indication of reduced vascular elasticity. Associated therewith is low blood flow of the coronary vessels and an increased risk of cardiac infarction. Low vascular elasticity promotes the deterioration of health in the case of chronic cardiac insufficiency. Vascular elasticity also influences the treatment possibilities of hypertension. Knowledge of the vascular elasticity and the changes thereof can optimize the type and dosage of drugs.

The pulse transit time can also be used to estimate the arterial blood pressure, or change in blood pressure, to the extent it is known over a sufficient period of time. Blood pressure is an important systematic variable. Changes in the mean blood pressure, changes in the stress-dependent rise in blood pressure, or blood pressure fluctuations, can be important indications of the development of a chronic diseases, such as arterial hypertension or cardiac insufficiency.

The concept of the invention results in a method for monitoring a thoracic property, wherein an electromedical implant is implanted epithoracically, comprising the following steps to be carried out by the implant: capturing a measurement signal associated with the thoracic property in the form of an impedance signal, and generating a parameter from the measurement signal that is indicative of the thoracic property; and determining an evaluation result on the thoracic property, wherein the measurement signal is captured in the form of an impedance signal using an electrode arrangement, which has at least one regular structure of a plurality of mutually isolated electrodes which are operatively connected by an impedance measuring unit, wherein an electrode body has an elongated shape.

A trigger unit can be provided in the monitoring system for the time-triggered activation of the communication module, for example, automatically, even-controlled, or patient- or physician-controlled. In this way, continuous or as-needed availability of the thoracic property for further processing into patient values, or for the analysis of a patient condition, can be ensured.

A processing unit can be provided in the monitoring system for processing or converting the evaluation result on the thoracic property into a data format indicating a patient condition and/or visualizing patient values. In the context of an indicating data format, for example, a parameter which is indicative of a critical condition of a patient can be represented. A visualizing data format is suited, for example, in order to visualize a critical parameter of a patient value in a particularly well-organized manner, such as in a histogram or in a color illustration.

The monitoring system furthermore can comprise an interrogation unit for the electromedical implant and/or the memory unit to query at least the evaluation result on the thoracic property. The interrogation unit can be part of a service center, or a patient device, or a physician device. All those involve can directly communicate with the monitoring system and/or the implant. The receiving unit can also be directly associated with a physician, or a patient, or a service enter.

Further advantageous refinements of the implant according to the invention will be apparent from the dependent claims and in detail provide advantageous possibilities for implementing the concept explained above in the context of the problem stated and also with respect to additional advantages.

The communication module for the wireless transmission of the evaluation result can be implemented in different manners. An implementation on inductive basis (using coil telemetry, for example), on electromagnetic basis (using electromagnetic waves in the radio frequency range, for example), or on acoustic basis (using ultrasound, for example) has proven particularly advantageous.

The electrode structure can comprise a plurality of electrodes for forming a number of poles, wherein the electrodes can be operated as electrodes interacting in pairs with each other by way of the impedance measuring unit. In this way, impedance measurements having different measuring configurations and optionally different information content can be implemented at the same time alternately or sequentially. In a preferred embodiment, a single pair of electrodes interacting with each other can be provided. This variant is suited above all for what is referred to as a two-pole measurement, wherein a voltage sampling and a current impression are carried out by way of the same electrodes. Advantageously, the electrode structure for forming three poles may comprise at least one electrode body which interacts in pairs with a first and a further electrode by way of the impedance measuring unit. This arrangement is advantageously suited for what is referred to as a three-pole measurement, wherein a voltage sampling is carried out via one of the current impression electrodes and at least one other electrode. Furthermore, an electrode structure which as proven advantageous is one in which two first poles are implemented by a first pair of electrodes and two further poles by a second pair of electrodes and they interact with each other in pairs by way of the impedance measuring unit. Such an arrangement is particularly suited for what is referred to as four-pole measurement, wherein a voltage sampling is carried by way of at least two electrodes not involved in a current impression.

A distance of the electrodes of a first electrode pair can be greater than a distance of the electrodes of a second electrode pair. Because a tissue scope is influenced by an impedance measurement, the impedance and therefore the conductivity of a tissue in the vicinity of the implant can be determined by way of the second pair of electrodes, while the first pair of electrodes is rather used to determine the impedance or conductivity of tissue that, viewed relative to the implant, affects deeper regions of the thorax.

In a similarly manner, as part of a refinement the electrode arrangement may comprise at least one electrode that is disposed close to the implant. The electrode disposed close to the implant in particular has the shape of the electrode structure. In addition, or as an alternative, the electrode disposed close to the implant can be configured in the shape of the housing of the implant. An electrode that is formed in the direct vicinity of the implant, which is to say on or with the housing, is suited in a particularly advantageous manner for measuring the impedance of the body tissue immediately surrounding the implant, such as for monitoring a epithoracic, peripheral blood flow.

An electrode arrangement which comprises an additional electrode that is disposed away from the implant as part of an electrode structure is also advantageous. Impedance measurements in deeper regions of the body tissue can be conducted when using an electrode that is disposed away from the implant. In this way, for example, the impedance can be used for determining a fluid condition in deeper regions. Such a fluid condition in deeper regions can be used for determining a further thoracic property, such as a fluid condition of the lungs or a cardiac blood flow. In addition, a signal correction can be achieved by subtracting an impedance signal for deeper regions of the tissue and an impedance signal for closer regions of the tissue from each other. For example, the impedance for determining the pulmonary fluid for deeper regions can be corrected by the impedance in the area surrounding the implant in order to compensate for fluctuations in the blood conductivity, such as due to hematocrit fluctuations. Conversely, the difference between impedance signals relating to a cardiac blood flow and an epithoracic, peripheral blood flow may be used to generate a parameter which is indicative of a time at which blood is ejected from the heart, and a second parameter which is indicative of a time of a blood pulse in the thoracic tissue.

A first electrode structure of the electrode arrangement can be formed on the housing and/or a second electrode structure of the electrode arrangement is formed on an electrode lead connected to the housing. The first electrode structure is preferably suited to form an electrode disposed close to the implant. The second electrode structure is preferably suited to form an electrode disposed away to the implant. An electrode close to the implant has a lesser distance from the implant than an electrode away from the implant.

An electrode body having an elongated shape can be produced in different ways within the context of the concept of the invention. An electrode structure comprising an electrode body having the shape of a strip electrode, which is to say an electrode having an elongated extension and a start and an end, has proven to be particularly advantageous. An electrode body can also be designed as an annular electrode surrounding a housing of the plant, for example the parts merging into each other in an annular shape or, having a helical shape. An electrode body having the shape of an interdigital electrode is also suited, which is known, for example, as a finger electrode or other interlocking electrode structure. The electrodes can be attached on a lateral surface, on a back, a front of the housing or on all sides of the housing—surrounding the same.

An electrode structure having a plurality of equidistant electrode bodies has proven to be particularly suited. Such an electrode structure advantageously has at least three equidistant electrode bodies. Three equidistant electrode bodies are suited advantageously for implementing a three-pole measurement. Four equidistant electrode bodies can advantageously be used for a four-pole measurement.

For an impedance measurement that is independent of the position of the implant, in particular a plurality of electrodes disposed symmetrically to the housing of the implant are suited. The electrodes can, in particular, be disposed on several sides, on all sides, or in an annular shape around a housing of the implant.

In an embodiment, a first electrode and/or a first electrode pair of the electrode arrangement can be controlled separately. In other words, a first electrode and/or a first electrode pair of the electrode arrangement can be controlled using a parameter that differs from a further electrode and/or a further electrode pair. The parameter, for example, can relate to a frequency and/or an amplitude and/or a phase for the impedance measurement.

Measuring the impedance (Z) denotes the measurement of a complex resistance, which as a real part and an imaginary part (Z=R+jX), which can also be expressed by way of the amount (|Z|; "amplitude") and phase ($\phi$). The impedance measuring unit can be designed such that, for example, it can impress a current having a defined exciter frequency (f) and measure the amount and phasing of the voltage with respect to the impressed current.

A first measurement signal in the form of a first impedance signal can be formed on the basis of a first exciter frequency, for example, and a second measurement signal in the form of a second impedance signal can be formed on the basis of a second exciter frequency. In this way, additionally dielectric properties of the tissue can be determined. Furthermore, information can be obtained from the dielectric properties of the tissue and can likewise be used to increase the sensitivity and/or specificity of the impedance measurement. Moreover, advantageously biochemical information can be obtained from the dielectric tissue properties, such as changes in the glucose level of the blood or a change in the hematocrit with diuresis.

A frequency variation can be carried out, for example, by way of a sinusoidal current having a variable frequency or by current pulses having variable pulse widths. A measuring frequency, or the variation of the measuring frequency, can range between 200 Hz and 10 GHz, for example.

A second exciter frequency can be provided for the second measurement signal that is lower than the first exciter frequency for the first measurement signal. Surprisingly, it was shown that at a comparatively high exciter frequency a temporal impedance curve be measured at which in particular the volume change of the heart can be captured well. After suitable frequency high-pass filtration, such an impedance curve having a higher exciter frequency can be used particularly advantageously to determine the time at which blood is ejected from the heart. In the present invention, for this purpose in particular the time at which a ventricular contraction starts can be determined.

In addition, it has been shown that at a comparatively low exciter frequency a temporal impedance curve can be measured which allows the blood flow of the tissue surrounding the implant to be captured, which is to say in particular a second measurement signal can be generated which is indicative of a time of a blood pulse in the thoracic tissue. After suitable frequency low-pass filtration, such an impedance curve can be used to determine the time of arrival of a blood pressure wave in a thoracic tissue.

According to a combination which refines the concept according to the invention in a particularly advantageous manner, a second measurement signal in the form of a second impedance signal is formed on the basis of a second exciter frequency and using an electrode close to the implant of the electrode arrangement, and a first measurement signal in the form of a first impedance signal is formed on the basis of a first exciter frequency and using an electrode away from the implant of the electrode arrangement, wherein the second exciter frequency is lower than the first exciter frequency.

A high frequency which is above the first and second exciter frequencies and at least in the MHz or GHz range can be used in particular for measuring a background impedance.

The detector arrangement can also comprises an ECG measuring unit including an electrode arrangement, which is equipped to detect, which is to say to subcutaneously measure, a thoracic property in the form of an electrocardiogram (ECG signal). If three or more electrodes are present, the ECG can be determined using several derivations. The ECG signal can be used, among other things, to diagnose the heart rate, QRS width, different types of tachyarrhythmia, syncopes and the like. For example, a T-wave alternans can be determined as a risk marker from the T-wave morphology. From the ECG signal, it is also possible to calculate the RR intervals for consecutive cardiac cycles. A time series analysis of consecutive RR intervals allows a determination of the heart rate variability and heart rate turbulence. In particular thoracic conductivity changes can be detected from the ECG signal, such as based on changes in the signal amplitude.

Based on the ECG signal, in combination with the impedance signal—specifically in accordance with the above special variant of the invention, while taking the above first parameter and second parameter of a first and second measurement signal into consideration—the pulse wave velocity can be determined, in order to make diagnostic assessments about the disease based on the condition of the arterial vessel. The pulse wave velocity can then be determined from the time difference between the R-wave of the QRS complex in the ECG signal and the volume pulse in the blood vessel reflected in the impedance signal.

The detector arrangement for capturing a thoracic property can comprise one or more of the detectors, for example, acoustic detectors, optical detectors, pressure and/or expansion detectors, acceleration detectors, temperature detectors, oxygen detectors, and/or biochemical detectors.

Using such and other detectors, a variety of additional useful information can be obtained about a thoracic property.

In particular an acceleration detector has proven advantageous. When using an acceleration sensor that is integrated in the implant housing, the activity of the patient and the change thereof can be observed. Activity information can be combined with an impedance and/or ECG signal, for example in order to differentiate resting and active phases and accordingly analyze results of the evaluation. Advantageously, an acceleration detector is designed as a three-axis sensor, so that the present body position of the patient can be determined, for example, when the position of the implant is known. On the basis of a three-dimensional acceleration signal, it can be detected when the patient falls. An acceleration detector can, at the same time, be configured as an acoustic detector if the band width thereof is sufficiently large in order to capture acoustic signals in the audible and superaudible frequency range.

An acoustic detector has been successfully applied in the form of a microphone, for example. An acoustic detector can be used to capture pulmonary and cardiac murmurs. Pulmonary, cardiac and respiratory murmurs, optionally in connection with the impedance measurement, and optionally also in connection with an ECG, can provide further indications for the detection of pulmonary edemas, apnea or other pulmonary diseases. Cardiac murmur can supply important diagnostic information, for example, it is known that the third heart sound can be used to monitor cardiac insufficiency. Based on the cardiac murmur, particularly when using the ECG measurement, valve closing times can be determined, for example.

Among the additional detectors mentioned above, in particular a temperature detector for measuring the body temperature of the living being has proven advantageous. An oxygen detector, such as in the form of an optical detector which is attached on or in the implant, can be advantageous for measuring the oxygen saturation in the surrounding tissue. Biochemical detectors likewise are advantageously integrated in the implant. Biochemical detectors may comprise sensors for glucose, electrolytes, hormones, or biomarkers and supply additional valuable information about the health of the patient.

Examples of the embodiments of the invention will be described in detail hereinafter with reference to the figures. The embodiments are not necessarily illustrated to scale, but instead the figures are provided as schematic drawings and/or in a slightly distorted form where it is desirable for explanation purposes. With respect to supplementary information for the teachings directly apparent from the figures, reference is made to the relevant prior art. It should be taken into consideration that a variety of modifications and changes relating to the shape and details of an embodiment can be made without deviating from the general concept of the invention. The characteristics of the invention disclosed in the specification, in the figures and in the claims can be essential for the refinement of the invention either alone or in any arbitrary combination with each other. In addition, any combination of at least two of the characteristics disclosed in the description, the figures and/or the claims falls within the scope of the invention. The general concept of the invention is not limited to the exact form or the details of the preferred embodiment shown and described hereinafter, and is not limited to a subject matter which would be limited in comparison with the subject matter claimed in the claims. If dimensional ranges are provided, the values within the tolerances listed shall also be disclosed as threshold values and can be used and claimed in any arbitrary manner. For the sake of simplicity, identical or similar parts, or parts having identical or similar functions, are denoted with the same reference numerals hereinafter.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
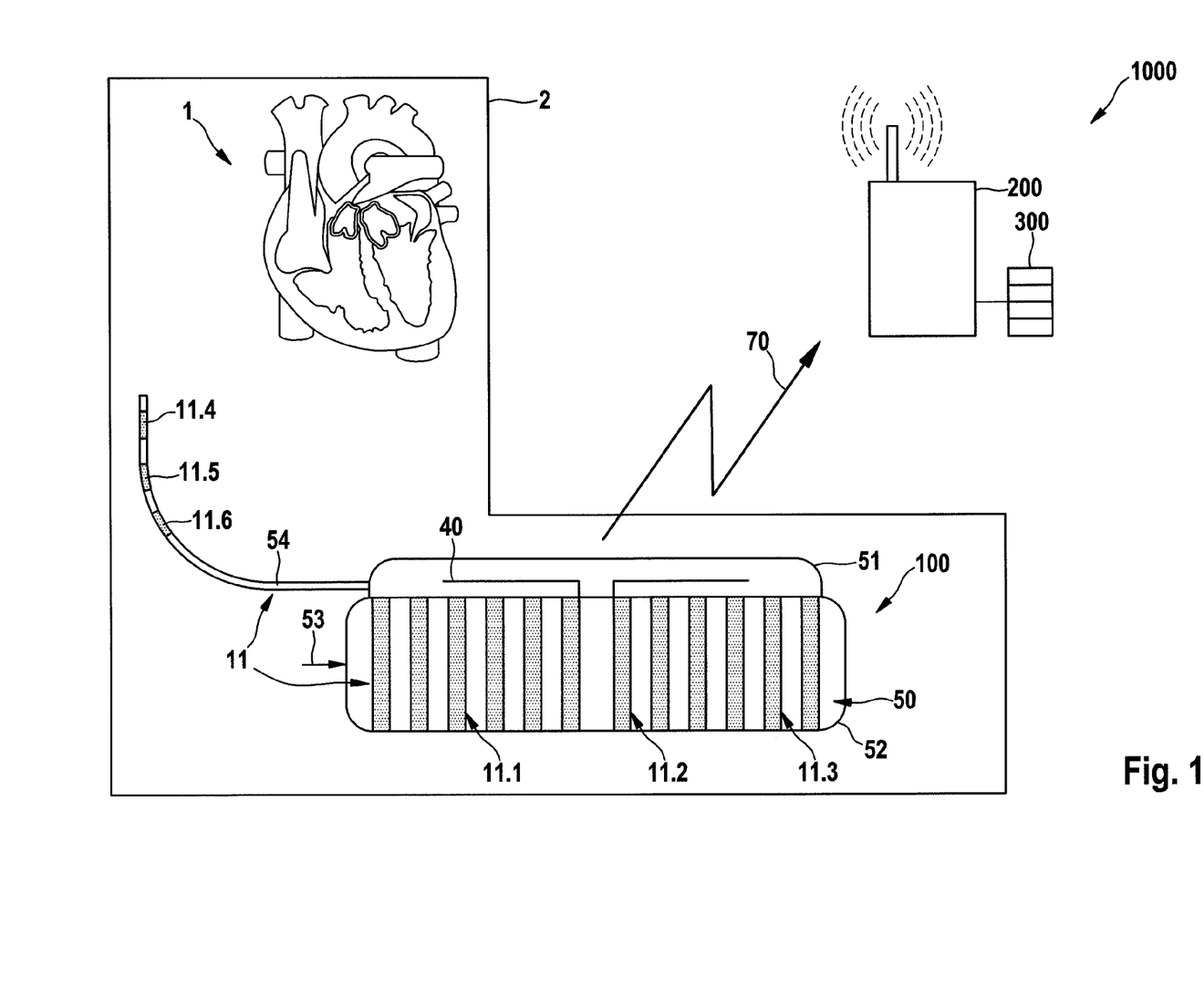
FIG. 1 illustrates a symbolic illustration of a monitoring system according to an embodiment of the invention in a symbolically illustrated thorax of a living being.

FIG. 1 shows a symbolic illustration of a preferred embodiment of a monitoring system 1000 comprising an electromedical implant 100, which is equipped to monitor a thoracic property of a living being, which is to say a patient with or without indications of cardiac insufficiency—the heart 1 of the patient and a thorax 2 of the patient are illustrated symbolically. In the present example, the implant 100 is designed purely as a monitoring implant, which is to say without therapeutic function. The implant 100 comprises a housing 50 having a housing container 52 and a header 51 and also an electrode arrangement 11 connected to the housing 50. The electromedical implant 100 can establish a wireless telemetry connection 70 to a receiving unit 200 of the monitoring system 1000 by way of a communication module 40, which is to say an RF antenna in the present example, disposed on the header 51. A parameter which is indicative of the thoracic property and/or an evaluation result from the parameter can thus be made available in a memory unit 300 of the monitoring system 1000. In this way, the evaluation result can be further processed by a processor unit, which is not explained in detail, in the monitoring system 1000, for example into additional patient values which are indicative of a patient's health. Such patient values can advantageously also be visualized, for example within the context of histograms, transient signals, or mean values, in order to clarify critical conditions of the patient to a physician, patient, or service center in the most intuitive and quickly discernible manner possible. In this way, alarm conditions can be made available to a physician, the patient, or the service center, in that the physician, the patient, or the service center has access to the memory 300 of the monitoring system 1000. In the present example, access to the monitoring system 1000 is enabled via a mobile or Internet-based network, which is not shown in detail. Individual patient values, or an individual patient condition, can be directly visualized for the physician, or the service center, or the patient, by way of Internet screens. In the present example, patient values are analyzed automatically in a service center, and critical conditions or a deterioration of a health condition, and the like, can be diagnosed and displayed to the physician. In some instances, such information can also be displayed in the receiving unit 200, of which a plurality are present, for example in the form of patient devices, physician devices, or other caretaker devices.

The monitoring system 1000 shown in the present example enables the remote monitoring of a thoracic fluid condition in a patient by way of the implant 100. Using an impedance measurement conducted by way of the electrode arrangement 11, conductivity changes in the thorax 2 of the patient are detected and thereby fluid accumulations are recognized, which can occur, among other things, as a result of developing cardiac decompensation. This relates in particular to fluid accumulations in the lungs of the patient. The impedance measurement is carried out by impressing an electric current, in the present example a pulse-shaped alternating current, having a constant amplitude, and by sampling a resulting voltage by way of the electrode arrangement 11 of the implant 100. For this purpose, respiratory information, which is to say a respiratory amplitude and frequency and based thereon a respiratory minute volume, are determined based on the impedance signal that is determined. Short-term signal fluctuations can be evaluated and, for example, sleep apnea can be detected or an apnea index can be calculated. In the present example, the detection of respiratory information in particular is used to synchronize the impedance measurement in the thorax 2 of the patient with the breathing cycle so as to eliminate the influence of the respiration on the impedance measurement. Furthermore, an epithoracic, peripheral ECG measurement is conducted by way of the electrode arrangement 11 as a subcutaneous ECG for determining a cardiac cycle. The impedance measurement as such can then also be synchronized with the cardiac cycle, thereby allowing cardiac cycle-dependent influences to be compensated for or analyzed.

The electrode arrangement 11 in the present example is provided in a first electrode structure having a plurality of mutually isolated electrodes 11.1, 11.2, 11.3, which are operatively connected by way of an impedance measuring unit and can be separately controlled and which can detect conductivity changes by way of an impedance measurement and therefore serve to indicate a fluid condition of the patient. The electrodes 11.1, 11.2, 11.3 close to the implant are mentioned by way of example for the collectivity of the electrodes of the first electrode structure on the housing 50 of the implant. An electrode body of the electrodes 11.1, 11.2, 11.3 has an elongated shape, such as a strip shape. The electrodes 11.1, 11.2, 11.3 of the first electrode structure in the present example are designed as annular electrodes and surround the housing container 52 of the housing 50 of the implant 100 in a ring shape. Such an annular electrode body has proven particularly suited for largely preventing positional influences of the implant 100 on an impedance measurement. An annular electrode can be disposed symmetrically to the implant, so that the impedance measurement for determining thoracic conductivity can be carried out regardless of a rotation of the implant 100 relative to the axis thereof. In addition, the implant 100 is provided with a reversible anchoring 53 in order to stabilize the position thereof and prevent migration of the implant 100.

The additional electrodes 11.4, 11.5, 11.6 provided for determining a subcutaneous ECG signal by way of a further epithoracic, peripheral impedance measurement are part of a second electrode structure, mutually isolated and operatively connected by way of the impedance measuring unit and provided on a lead 54 disposed on the header 51. All electrodes 11.1, 11.2, 11.3 of the first electrode structure and all electrodes 11.4, 11.5, 11.6 of the second electrode structure are preferably, but not necessarily, disposed equidistant relative to each other. Due to the proximal positions of the electrodes 11.1, 11.2, 11.3 of the first electrode structure, an epithoracic, peripheral impedance can be determined particularly well by the implant 100. For the epithoracic, peripheral impedance measurement by the first electrode structure a tissue scope is used which is located largely in the direct vicinity of the implant 100, associated with the range of an impressed current or sampled voltage signal in the tissue surrounding the implant. In contrast, the three electrodes 11.4, 11.5, 11.6 of the second electrode structure connected via the lead 54 are provided as electrodes away from the implant and can determine a cardiac, subcutaneous ECG. Because there are three electrodes, the ECG can also be determined using several derivations.

In addition to the impedance measurement by way of the first electrode structure, thoracic conductivity changes can also be concluded from the ECG signal—in addition to typical patient values such as heart rate, QRS width, different types of tachyarrhythmia, syncopes, T-wave morphology and R-intervals. In the present example, this is done on the basis of changes of the ECG signal amplitude. In this functional position, the electromedical implant 100—on the basis of an impedance measurement for the thoracic conductivity determination of a patient—is used to detect a fluid accumulation in the thorax 2 of the patient at an early stage.

Figure 2:
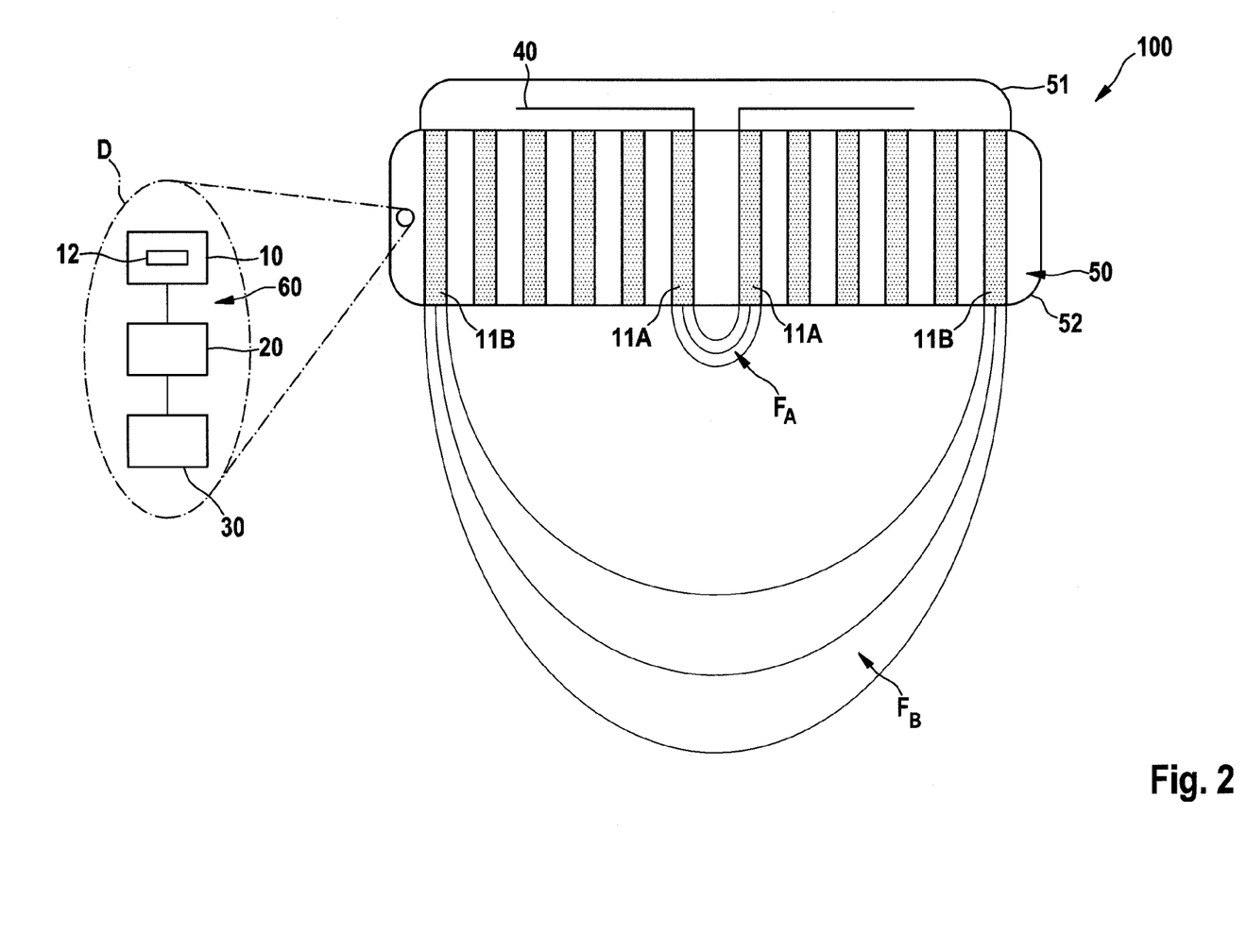
FIG. 2 illustrates an electromedical implant in the monitoring system of FIG. 1 in a particularly preferred functional position, which is to say comprising electrode pairs which includes electrodes having different distances, wherein the electrode pairs can be used with impedance measurements at different frequencies, thereby achieving different measuring ranges.

FIG. 2 shows a particularly preferred first functional setting of the first electrode structure, wherein the electrodes of a first electrode pair 11A and electrodes of a second electrode pair 11B are operatively connected by way of the impedance measuring unit, which is to say they are used to form a pole pair for a two-pole measurement. A current is impressed and a voltage is sampled by way of the electrodes of the electrode pair 11A—the same applies to the electrode pair 11B. Compared to the electrodes of the second electrode pair 11B, the electrodes of the first electrode pair 11A have smaller distances. As a result, the flux lines FA of a voltage curve of the first electrode pair 11A effective for the impedance measurement, which are shown by way of example, have only a comparatively small penetration depth into the tissue—compared to analogous flux lines FB of the second electrode pair 11B. This circumstance alone already allows the impedance in the direct vicinity of the implant to be determined using an impedance measurement by way of the first electrode pair 11A. Using an impedance measurement by way of the second electrode pair 11B, an impedance in deeper regions of the body tissue is measured. In the present example, the impedance for determining the pulmonary fluid for deeper regions can be corrected by the impedance in the area surrounding the implant in order to compensate for fluctuations in blood conductivity, such as due to hematocrit fluctuations.

In an even more sophisticated impedance measurement, an impedance measurement by way of the first electrode pair 11A is carried out a lower frequency than an impedance measurement by way of the electrode pair 11B. In the present example, the impedance measurement by way of the electrode pair 11A is carried out at 2 kHz, while the impedance measurement by way of the electrode pair 11B is carried out at 20 kHz. The impedance signals can be separated using a frequency low-pass filter for the electrode pair 11A and using a frequency high-pass filter for the electrode pair 11B. It has been shown that the low-frequency impedance signal portion can be indicative of a time of a blood pulse in the thoracic tissue directly surrounding the implant.

In a modified second functional position, the impedance signal curve, which is obtained by the first electrode pair 11A, can be used to determine the time of arrival of a blood pressure wave in a thoracic vessel. Moreover, it has been found that the time at which blood is ejected from the heart, which is to say in the present example the time at which a ventricular contraction starts, can be determined from the impedance signal curve at a higher frequency. This circumstance is due to the penetration of the flux lines FB relevant for the impedance measurement into deeper regions of the thorax, in comparison with the flux lines FA of the impedance measurement by way of the first electrode pair 11A.

The pulse transit time delta-t ($\Delta t$) can be determined from the difference between the time tgef of arrival of a blood pressure wave in a thoracic vessel and the time tsys at which blood is ejected from the heart. The pulse transit time is a good indicator of the condition of a vessel or of a blood pressure of the patient. In the second functional position described above with frequency-dependent impedance measurement by the electromedical implant, in this way an assessment can be made of a cardiac blood flow and an epithoracic, peripheral blood flow in order to determine the pulse transit time.

In a third functional position of the electromedical implant 100, which is apparent from the design according to FIG. 1, a conclusion of the pulse transit time can also be drawn. For this purpose, the time at which blood is ejected from the heart, which is to say the start of the ventricular contraction, is determined from an R-wave or the QRS complex of the ECG signal—the latter being measured by way of the electrodes 11.4, 11.5, 11.5 of the second electrode structure at the lead 54. Additionally, a time of the arrival of a blood pulse in the thoracic tissue, which can be obtained from the impedance measurement of the electrodes 11.1, 11.2, 11.3 of the first electrode structure, can be used to determine a pulse transit time—again from the difference between the times.

Overall, different, and in particular three, of the above functional positions of the electromedical device can be set using the measurement and control electronic system 60 of the implant 100 illustrated in the enlarged detail D. The measurement and control electronic system 60 of the implant 100 in particular comprises a detector arrangement 10, which includes an impedance measuring unit 12 and is configured together with the electrode arrangement 11, which is to say the electrodes of the first electrode structure and of the second electrode structure, to capture a measurement signal associated with the thoracic property in the form of an impedance signal and/or ECG signal. The measurement and control electronic system 60 further comprises a monitoring arrangement 20, which is connected to the detector arrangement 10 and equipped to generate a parameter from the measurement signal that is indicative of the thoracic property. The thoracic property in the first functional position of the electromedical implant 100 is a conductivity of the thorax 2 for determining a fluid condition of the patient. In the second and third functional positions, it is a parameter of a cardiac or epithoracic, peripheral impedance measurement signal, which indicates a time at which blood is ejected from the heart and/or a time of arrival of a blood pulse in the thoracic tissue.

An evaluation unit 30, which is equipped to quantify an evaluation result regarding the thoracic property from the parameter, is connected to the monitoring arrangement 20. In the case of the first functional position, this can be an evaluation result in the form of a quantifiable thoracic fluid volume. In the case of the second or third functional position of the electromedical implant, this can be a pulse transit time $\Delta t$, which is obtained by subtracting a time at which blood is ejected from the heart and a time of arrival of a blood pulse in the thoracic tissue.

In summary, the invention relates to an electromedical implant 100 for monitoring a thoracic property of a living being, including a detector arrangement 10 comprising an impedance measuring unit 12 and an electrode arrangement 11 for capturing a measurement signal associated with the thoracic property in the form of an impedance signal; a monitoring arrangement 20, which is connected to the detector arrangement and equipped to generate a parameter from the measurement signal that is indicative of the thoracic property, and an evaluation unit 30, which is equipped to quantify an evaluation result regarding the thoracic property based on the parameter, is connected to the monitoring arrangement 20. To this end, the electrode arrangement 11 comprises at least a plurality of mutually isolated electrodes 11.1, 11.2, 11.3, which are disposed on the housing and operatively connected by way of the impedance measuring unit 12 and which can be separately controlled, wherein an electrode body has a strip shape.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. An electromedical implant for monitoring a thoracic property of a living being, the implant comprising:
   a housing;
   a detector arrangement including an impedance measuring unit and an electrode arrangement, which are configured to capture a measurement signal associated with the thoracic property in the form of an impedance signal;
   a monitoring arrangement connectable to the detector arrangement and configured to generate a parameter from the measurement signal that is indicative of the thoracic property, and
   an evaluation unit connectable to the monitoring arrangement and configured to determine an evaluation result regarding the thoracic property from the parameter,
   wherein the electrode arrangement comprises a plurality of mutually isolated electrodes that are disposed on the housing and operatively connected via the impedance measuring unit and that are separately controllable,
   wherein an electrode body has a strip shape, and
   wherein an output of the impedance measuring unit is directly connected to an input of the monitoring arrangement.

2. The electromedical implant according to claim 1, wherein the impedance measuring unit includes an exciter module for delivering an electric current via the electrode arrangement and a sampling module configured to receive a voltage via the electrode arrangement.

3. The electromedical implant according to claim 1, further comprising a communication module configured to wirelessly transmit the evaluation result in an evaluation signal.

4. The electromedical implant according to claim 1, wherein, for forming a plurality of poles, the implant further comprises a plurality of electrodes, which are operated in pairs as operatively connected electrode pairs via the impedance measuring unit.

5. The electromedical implant according to claim 1, wherein a distance of the electrodes of a first electrode pair is greater than a distance of the electrodes of a second electrode pair.

6. The electromedical implant according to claim 1, wherein the electrode arrangement comprises at least one electrode disposed close to the implant, and/or a second electrode disposed away from the implant as part of an electrode structure.

7. The electromedical implant according to claim 1, wherein the electrode arrangement comprises at least one electrode disposed away from the implant, wherein the second electrode disposed away from the implant is part of a further electrode structure.

8. The electromedical implant according to claim 1, wherein a first electrode structure of the electrode arrangement is formed on the housing and/or a second electrode structure of the electrode arrangement is formed on an electrode lead connected to the housing.

9. The electromedical implant according to claim 1, wherein the electrode structure is formed by an electrode body in the shape of a strip electrode, an annular electrode, or an interdigital electrode.

10. The electromedical implant according to claim 1, wherein a first electrode and/or a first electrode pair of the electrode arrangement is controllable separately using an electric frequency and/or amplitude and/or phase that is different from a further electrode and/or electrode pair.

11. The electromedical implant according to claim 1, wherein a first measurement signal in the form of a first impedance signal is formed on the basis of a first exciter frequency, and/or a second measurement signal in the form of a second impedance signal is formed on the basis of a second exciter frequency.

12. The electromedical implant according to claim 1, wherein the electrode arrangement comprises at least three electrode bodies.

13. The electromedical implant according to claim 1, wherein the plurality of electrodes are disposed symmetrically to a housing container of the implant, and are disposed on several sides of, or all sides of, or in an annular shape around a housing container of the implant.

14. The electromedical implant according to claim 1, wherein the detector arrangement for capturing the measurement signal comprises an ECG (electrocardiogram) measuring unit including an electrode arrangement, which is equipped to detect the measurement signal in the form of an ECG signal.

15. The electromedical implant according to claim 1, wherein the detector arrangement for capturing a thoracic property comprises one or more detectors, the detectors being an acoustic detectors, optical detectors, pressure and/or expansion detector, acceleration detectors, temperature detectors, oxygen detectors, and/or biochemical detectors.

16. A monitoring system, comprising the electromedical implant according to claim 1, comprising:
   a communication module configured to wirelessly transmit the evaluation result in an evaluation signal from the implant;
   a receiving unit configured to receive the evaluation signal; and
   a memory unit configured to store the evaluation result.

17. The electromedical implant according to claim 1, wherein the plurality of electrodes are annular electrodes each having a ring shape that surrounds the housing.

18. The electromedical implant according to claim 1, wherein the housing includes a housing container and a header, and
   wherein the plurality of electrodes are disposed on the housing container of the housing.

19. The electromedical implant according to claim 18, wherein a communication module is provided in the header of the housing.

20. The electromedical implant according to claim 18, wherein the plurality of electrodes includes at least two electrode pairs, both of the at least two electrode pairs being disposed on the housing container.

21. The electromedical implant according to claim 20, wherein a distance between each electrode of a first electrode pair of the at least two electrode pairs is smaller than a distance between each electrode of a second electrode pair of the at least two electrode pairs.

* * * * *